United States Patent
Zellerhoff

(10) Patent No.: US 7,852,984 B2
(45) Date of Patent: *Dec. 14, 2010

(54) METHOD AND DEVICE FOR THE SEPARATE THREE-DIMENSIONAL REPRESENTATION OF THE ARTERIAL AND VENOUS VASCULAR SYSTEM USING C-ARM ANGIOGRAPHY SYSTEMS

(75) Inventor: Michael Zellerhoff, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/494,687

(22) Filed: Jun. 30, 2009

(65) Prior Publication Data

US 2009/0262897 A1    Oct. 22, 2009

Related U.S. Application Data

(63) Continuation of application No. 11/897,373, filed on Aug. 30, 2007, now Pat. No. 7,558,372.

(30) Foreign Application Priority Data

Aug. 31, 2006    (DE) ................ 10 2006 040 934

(51) Int. Cl.
  *H05G 1/64* (2006.01)

(52) U.S. Cl. .............. 378/98.12; 378/9; 378/116
(58) Field of Classification Search .............. 378/4, 378/9, 98.12, 114–116; 382/131, 132
See application file for complete search history.

(56) References Cited

U.S. PATENT DOCUMENTS

| 7,020,235 | B2 | 3/2006 | Hornegger et al. |
| 2003/0169911 | A1 | 9/2003 | Snyder et al. |
| 2005/0046644 | A1 | 3/2005 | Ohishi |

FOREIGN PATENT DOCUMENTS

| DE | 102 41 184 A1 | 4/2004 |
| EP | 1 510 972 A2 | 3/2005 |

*Primary Examiner*—Jurie Yun

(57) ABSTRACT

The invention relates to a method and a device for the separate three-dimensional representation of arteries and/or veins in a vascular system of the body by means of a C-arm biplanar system having two C-arms, which can each record a sequence of x-ray images from different projection angles during a mask or filler pass. With the filler pass, both C-arms record x-ray images, so that the x-ray images of the filler pass can be combined to form a first data record, which contains x-ray images from the arterial phase of the vascular contrasting and/or to form a second data record, which contains x-ray images from the venous phase of the vascular contrasting. This enables the arterial and venous phases to be reconstructed separately.

15 Claims, 1 Drawing Sheet

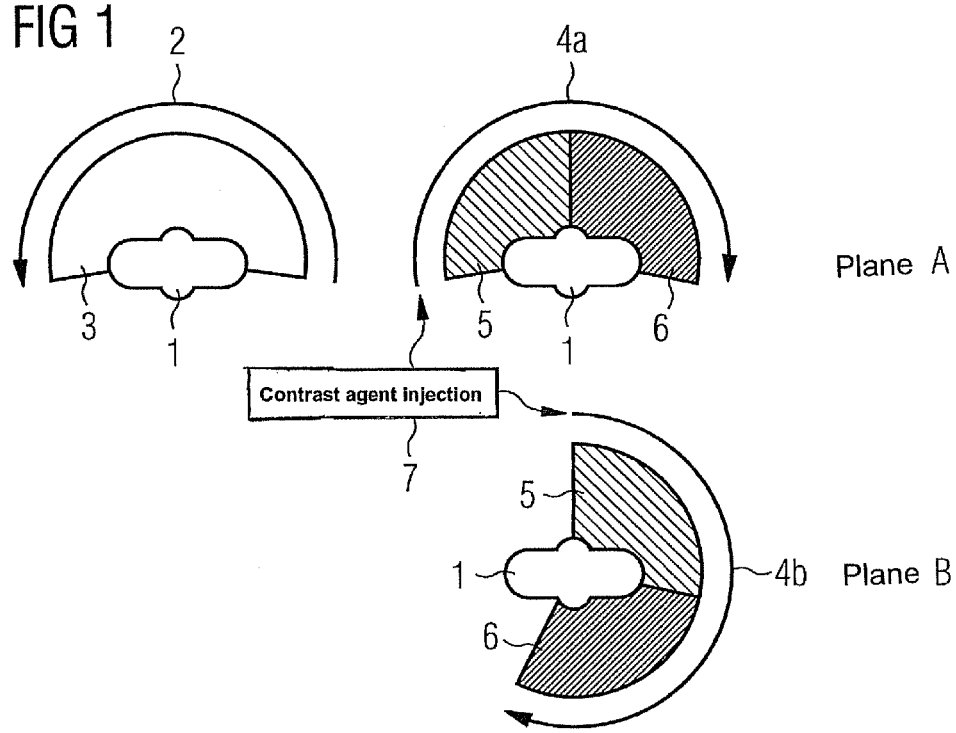
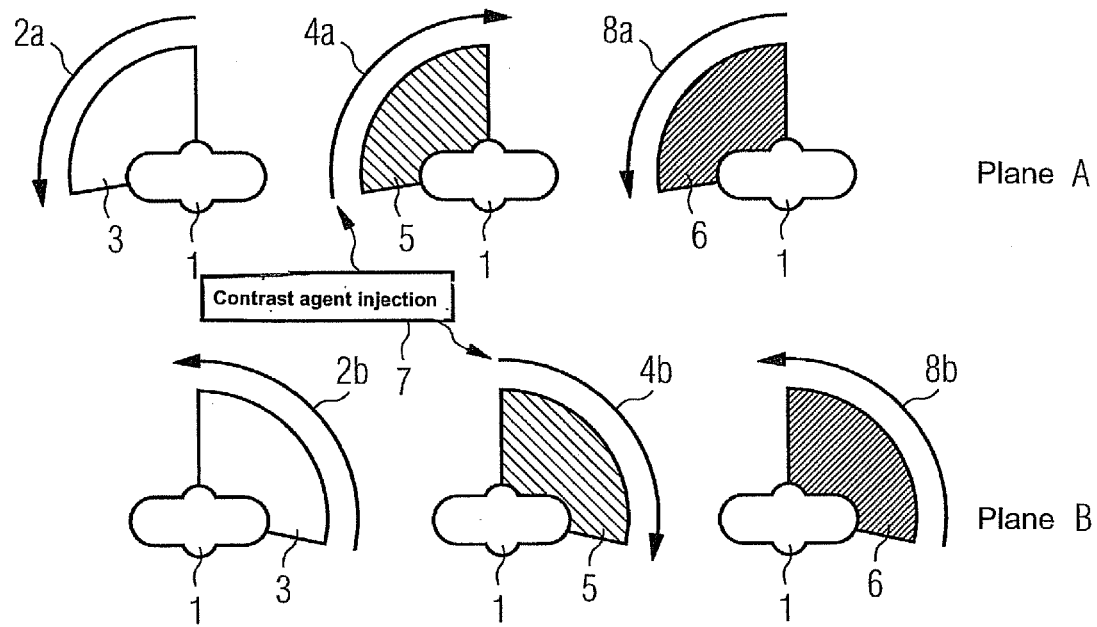

METHOD AND DEVICE FOR THE SEPARATE THREE-DIMENSIONAL REPRESENTATION OF THE ARTERIAL AND VENOUS VASCULAR SYSTEM USING C-ARM ANGIOGRAPHY SYSTEMS

CROSS REFERENCE TO RELATED APPLICATIONS

This application is a continuation of U.S. application Ser. No. 11/897,373 filed Aug. 30, 2007 now U.S. Pat. No. 7,558,372. This application claims priority of German application No. 10 2006 040 934.5 filed Aug. 31, 2006, which is incorporated by reference herein in its entirety.

FIELD OF THE INVENTION

The present invention relates to a method for the separate three-dimensional representation of arteries and/or veins of a vascular system in a part of the body of a vertebrate using a C-arm biplanar system, in other words an x-ray angiography system having two C-arms which can be moved about a patient bed, into which an x-ray recording system is integrated in each instance.

BACKGROUND OF THE INVENTION

There is an increasing demand for the most accurate possible three-dimensional representation of the appearance and pattern of vessels in parts of the body, in particular of arteries and veins, for diagnostic purposes within the field of vascular diseases and the therapy thereof. The examination of cerebral aneurysms represents an important field of application, this also includes an analysis and optimal representation for defining the aneurysm neck using topographical relations with adjacent vessels. Angiographs are also carried out on different parts of the body, in order to determine arteriosclerotic changes or deformities. The introduction of computer-aided rotation angiography, which reconstructs three-dimensional representations with an equal resolution from the projection raw data, achieves a technical breakthrough within the field of diagnostics. The so-called C-arm angiographs form here the prior art, in which an x-ray source and an x-ray detector arranged on a C-arm and opposite thereto, are rotated about the part of the body of a patient to be examined in an arc encompassing approximately 200° and between 50 and 500 x-ray images are recorded here and digitally stored. A three-dimensional model of the x-rayed part of the body can be calculated from x-ray images recorded from different projection angles. The conventional 3D angiography nevertheless fails to ensure an adequately clear separation between the arterial and venous vascular systems, by virtue of the recording times and the dynamics of the contrast agent propagation.

With the afore-described three-dimensional vascular representation, a so-called mask pass and a filler pass are recorded. During the "mask pass", the C-arm rotates about the part of the body of the patient or the whole patient and records a first sequence of x-ray images without contrasting over the predetermined angular range. A contrast agent is then injected into the vessel of interest and with another C-arm rotation, the so-called "filler pass", a second sequence of x-ray images is recorded. The two sequences are now subtracted from each other such that only the contrasted vessels (i.e. containing contrast agent) can still be seen in the result. These are now reconstructed to form a three-dimensional image data record using a 3D reconstruction method. Alternatively, masks and filler pass sequences can also be reconstructed separately and the resulting three-dimensional data records are subtracted from one another.

The 3D angiography method according to the prior art generally provides a three-dimensional image data record, which represents both a part of the arterial vascular system as well also as parts of the venous vascular system. The reason for this flaw in current angiography systems can be attributed to the rotation time of the C-arm of 5 s being significantly longer than the arterial phase of the vascular contrasting, which only lasts 2 to 3 seconds. The contrast agent then permeates over the conventional capillary paths into the venous vascular system so that a venous phase of the vascular contrasting is indicated after the arterial phase has passed, said vascular contrasting being characterized in a subsequent part of the rotation of the tomographs, thereby resulting in a three-dimensional mixed structure of arteries and veins.

DE 102 41 184 A1 discloses a method for generating a volume data record of an object using a first and a second x-ray system, with which a first series of 2D projections of the object is recorded with the first x-ray system at projection angles which differ from one another, with the first x-ray system being rotated about an axis and scanning a first angular range, and with which a second series of 2D projections of the object are essentially recorded at the same time using the second x-ray system at different projection angles from one another, with the second x-ray system being rotated about an axis and scanning a second angular range which differs from the first angular range.

SUMMARY OF THE INVENTION

The object underlying the present invention is thus to generate three-dimensional image data records of vessels, which either only represent arteries or veins (depending on requirements).

This object is achieved in accordance with the invention by the method for the separate three-dimensional representation of arteries and/or veins as well as the device for separate three-dimensional representation as claimed in the independent claims.

Further advantageous embodiments, aspects and details of the present invention result from the dependent claims, the description and the appended drawings.

The knowledge underlying the invention is that twice as many x-ray images can be acquired simultaneously using a C-arm biplanar system, in other words an x-ray angiography system with two C-arms, than with a monoplanar system, even though the readout speed of the x-ray detector and the rotation speed of the C-arm are equally as great. The recording time for a single filler pass is thus halved compared with a monoplanar system. It is thus possible to record and reconstruct an arterial phase of approximately two to three seconds (with current conventional rotation times of four to five seconds per pass) in an isolated fashion.

In a first aspect, the invention is thus directed at a method for the separate three-dimensional representation of arteries and/or veins of a vascular system in a part of the body of a vertebrate using a C-arm biplanar system, comprising two C-arms, each of which can record a sequence of x-ray images from different projection angles during a mask pass or a filler pass about the part of the body. The method is characterized by the following steps:

(a) Implementing a mask pass about a body part to be examined prior to injecting contrast agent into the vertebrate, in which at least one of the two C-arms records x-ray images;

(b) Implementing a filler pass about the part of the body after injecting a contrast agent, in which the two C-arms of the biplanar system in the rotation direction are offset against one another by a differential angle, and in which x-ray images are recorded with both C-arms;

(c) Combining the x-ray images of the filler pass of the first and the second C-arm to form a first data record, which contains x-ray images from the arterial phase of the vascular contrasting and/or to form a second data record, which contains x-ray images from the venous phase of the vascular contrasting; and (d) Subtracting the data record obtained during the mask pass from one of the first and/or second data records obtained during the combination, in order to obtain at least one final data record, which contains data relating to a three-dimensional representation of the arterial or venous vascular system.

In terms of the present invention, a mask pass is a rotation pass of the C-arm x-ray device without the use of a contrast agent.

A filler pass is understood in accordance with the invention to mean a rotation pass of the C-arm x-ray device, in which the cavity to be examined, in this case vessels, are filled with a contrast agent to such a degree that an adequate x-ray contrast results.

As is known to experts, a contrast agent is a substance, which is relatively impermeable for x-rays and thus makes filled vessels visible by a clear x-ray shading.

An injection of contrast agent is understood to mean the administration of the contrast agent into the cavity to be examined and/or the vessel to be examined, by means of an injection for instance.

A combination of data from the filler passes to form data records is understood to mean that sub quantities of the x-ray images of the two C-arms can be combined to form new data records, according to predetermined rules, which only contain x-ray images from the arterial and/or venous phase of the vessel contrasting, with the aid of a predetermined algorithm and if necessary under the influence of a human evaluator. This can be achieved for instance in that the first half of the x-ray image sequence of each C-arm is assigned to the arterial phase and the second half is assigned to the venous phase in each instance.

The differential angle between the two C-arms of the biplanar system is particularly preferred at least during the filler pass of approximately 90° plus the half fan angle of the C-arms. As a three-dimensional image data record can already be reconstructed from an x-ray sequence, which covers 180° plus the fan angle of the C-arm, a complete data record can already be recorded with this differential angle with a rotation of the C-arm about 90° plus the half fan angle. The recording time is thus halved for an individual pass compared with the monoplanar system.

With the method according to the invention, as with the current conventional monoplanar systems and also with the biplanar system, a mask pass is first recorded without a contrast agent. For the mask pass, either both C-arms can be rotated in each instance about 90° plus the half fan angle or only one C-arm is rotated about 180° plus the fan angle. After injecting a contrast agent, a rotation is carried out with both C-arms which is potentially delayed by a certain time, during which the contrast agent permeates into the part of the body of interest. If the two C-arms are offset against one another by 90° plus the half fan angle, a rotation by 90° plus the half fan angle is preferably carried out. The x-ray images recorded by the two C-arms during this filler pass can be combined to form a first data record, and thus produce a complete data record, from which a three-dimensional image data record can be reconstructed in the arterial phase. A three-dimensional image of the arterial vascular system is now obtained by subtracting the mask pass from the filler pass and subsequently reconstructing, or by reconstructing the mask pass and the filler pass and then subtracting.

A further rotation of both C-arms about approximately 90° plus the half fan angle can preferably be carried out immediately after the arterial filler pass has been recorded. This rotation can be carried out both in the same direction as well as in an opposite direction, such as the first rotation of the filler pass. The x-ray images of the two C-arms thus obtained can be combined in a similar manner to form a reconstructable second data record, which contains the venous phase of the vascular contrasting. A three-dimensional image data record of the venous vascular system can be reconstructed from this data record, as described above.

Alternatively to the above-described embodiment, in which the C-arms, during the filler pass, rotate in each instance only about approximately 90° plus the half fan angle, the filler pass can also include a rotation of the two C-arms about approximately 180° plus the whole fan angle of the C-arms. In this way, the x-ray images of the first 90° plus the half fan angle of both C-arms are combined to form a first data record of the arterial phase, the images of the second 90° plus the half fan angle are combined to form a second data record of the venous phase.

A mask pass is likewise also conceivable, in which both C-arms rotate about 180° plus fan angle, with images only being recorded with one of the two C-arms.

In a preferred embodiment, the examined body part is a skull of a person. One important field of application is herewith the locating of aneurysms in the vessels of the brain. It is however clear that other parts of the human body and other types of animal can essentially be accessed using a vascular system according to the method of the invention. The method has been restricted in accordance with the invention to vertebrate, since these have a separate arterial and venous blood circulation, nevertheless it is clear that if necessary the method can also be applied with other classes of animal, provided these have a contrastable vascular system with arteries and veins.

In a further aspect, the invention is directed towards a device, with all that has been said in respect of the method also being valid to the device or vice versa, so that reference can be made alternately. The device according to the invention for separate three-dimensional representation of arteries and/or veins of a vascular system in a part of a body of a vertebrate comprises a C-arm biplanar system, which comprises two C-arms, which are designed to record a sequence of x-ray images from different projection angles in each instance during a mask or filler pass about the body part and is characterized by:

(a) a device for injecting a contrast agent into the vertebrate;

(b) a control device for controlling the two C-arms of the biplanar system such that a mask pass about a part of the body to be examined is first carried out without contrast agent, and then a filler pass is carried out after injecting the contrast agent, in which the two C-arms of the biplanar system are offset against one another in the rotation direction about a differential angle and whereby the x-rays are recorded using both C-arms.

(c) a data storage device for storing the x-ray images obtained during the mask pass and during the filler pass;

(d) a computing module for combining x-ray images of the filler pass from the first and the second C-arm to form a first data record, which contains x-ray images from the arterial phase of the vascular contrasting and/or to form a second data record, which contains x-ray images from the venous phase of the vessel contrasting; and for subtracting the data record obtained during the mask pass from a first and/or second data record obtained during the combination in order to obtain at least one final data record, which contains data for a three-dimensional representation of the arterial or venous vascular system.

The device for injecting a contrast agent is preferably an automatic injector, with which the time instant and the speed of the injection can be precisely determined.

A control facility is the control module of a C-arm biplanar system for instance. This can be integrated for example into a PC or suchlike.

A computing module is understood here to mean either a device, which is designed especially to perform calculations to be carried out, for instance an analog computer or a digital signal processor with a corresponding controller, or a computer module is understood to mean a software program product, which implements the functionalities on a universal computing system. A data memory device is understood to mean any device which is able to store digital data, be this a volatile or permanent main memory, a hard disk, an optical data carrier etc. with access hereto being possible by the computing modules.

In a particularly preferred embodiment, the device is suited to implementing the method according to the invention.

BRIEF DESCRIPTION OF THE DRAWINGS

The invention is to be described in more detail below with reference to concrete exemplary embodiments, with reference being made to appended drawings, in which the following is illustrated:

FIG. 1 shows the principle of the scanning of a patient body in a first embodiment of the invention, FIG. 2 shows the principle of the scanning of a patient body in a second embodiment of the invention.

DETAILED DESCRIPTION OF THE INVENTION

According to the first embodiment of the method according to the invention, a rotation pass (mask or filler pass) of the C-arm biplanar system comprises approximately 180° plus the fan angle in each instance. In the illustration in FIG. 1, the upper row "plane A" shows the recording from the view of the first C-arm, the lower row "plane B" shows the recordings of the second C-arm, which, in the example shown, is offset compared with plane A by a differential angle of approximately 90° plus a half fan angle, namely in the rotation direction.

In the left upper sub image of FIG. 1, the mask pass is shown schematically. This indicates a cross-sectional view of a patient 1. The arrow 2 shows the rotation direction of the first C-arm and sector 3 shows the detected projection angle of the mask pass. A complete rotation pass about approximately 180° plus the fan angle is carried out counter clockwise, with only the first C-arm (plane A) recording x-ray images. The second C-arm can rotate or be stationary.

A filler pass is illustrated on the right-hand side, in which both C-arms (Plane A and plane B) participate. At the start, a contrast agent is injected at time instant 7. Consequently, both C-arms rotate in the direction of arrows 4a, 4b in a clockwise direction about approximately 180° plus the fan angle. During the first half of this filler pass, the arterial phase 5 is detected, which is shown by a shaded sector 5 on the left. In the further course of this filler pass, the venous phase is used, which is shown in each instance by a shaded sector 6 on the right.

As is clear from FIG. 1, the sectors 5 of planes A and B can be combined to form a complete data record, which covers more than 180°, namely 180° plus the fan angle. A three-dimensional image of the arterial phase can thus be reconstructed from the x-ray images recorded in the sectors 5. The same applies to the venous phase and the two sectors 6, which can, as a whole, be combined to form a reconstructable data record.

The embodiment in FIG. 1 thus requires two rotations of the biplanar system about 180° plus the fan angle in each instance. These can, as shown, occur in the opposite direction, they can however also occur in the same direction. The system must however then rotate once by 360° about the patient 1, thereby potentially running into spatial difficulties.

The embodiment in FIG. 2 by contrast only requires 90° rotations. This exemplary embodiment is thus preferable for systems which only allow a restricted rotation angle.

Both C-arms rotate about 90° plus the half fan angle in order to record the mask pass, as shown in both left illustrations of planes A and B in FIG. 2. During the rotation in the direction of arrows 2a and 2b, each C-arm records a sector 3 of x-ray images in each instance, which are subsequently combined to form a complete mask pass. After the contrast agent injection 7, both C-arms counter rotate about 90° plus the half fan angle along the arrows 4a, 4b in the opposite direction and herewith record the images of the arterial filler pass along the sectors 5. The images of both sectors 5 can, as shown in exemplary embodiment 1, be combined to form a complete first data record in each instance, which contains x-ray images only from the arterial phase of the vascular contrasting.

As shown in both right sub images, the two C-arms then rotate back in a further rotation about 90° plus the half fan angle in the same direction as with the mask pass along arrows 8a, 8b and in doing so record x-ray images of the venous phase along the sectors 6. The x-ray images of sectors 6 are then combined to form a second data record, which contains x-ray images from the venous phase of the vascular contrasting. It is thus possible to obtain two final data records by subtracting the data record 3 obtained during the mask pass 2a, 2b, from the arterial data record of sectors 5 and the data record of sectors 6, said two final data records containing x-ray images which can be reconstructed to form a three-dimensional image data record of the arterial and/or venous vascular system. Alternatively, as mentioned above, the individual data records of the mask pass, the arterial and venous phase can also be reconstructed first to form a three-dimensional image data record, these subsequently being subtracted from one another.

The method according to the invention enables, with the aid of a C-arm biplane system, recording times for a reconstructable data record comprising x-ray images to be realized in less than 3 seconds. This enables three-dimensional image data records of the arterial and venous vascular system to be obtained without mutual superimposition.

The invention claimed is:

1. A method for obtaining a separate x-ray data record of arteries or veins of a vascular system in a part of a body of a vertebrate using a biplanar C-arm system with a first C-arm and a second C-arm, comprising:

recording a mask pass x-ray data record of the part of the body during a mask pass of the C-arm system rotating in a first direction about the part of the body prior to injecting a contrast agent into the vertebrate;

recording a first and a second filler pass x-ray data records of the part of the body during one filler pass of the C-arm system rotating in a second direction opposite to the first direction about the part of the body respectively recorded by the first and the second C-arms after injecting the contrast agent into the vertebrate, wherein the first and the second C-arms are offset with respect to each other about a differential angle in the rotation direction;

combining the first and the second filler pass x-ray data records to generate a first data record only comprising x-ray data records of the arteries and to generate a second data record only comprising x-ray data records of the veins; and subtracting the mask pass x-ray data record from the first or the second data record to obtain the separate data record of the arteries or the veins for medically examining the part of the body, wherein the filler pass comprises a rotation of the C-arms about 180° plus a fan angle of the C-arms.

2. The method as claimed in claim 1, wherein a first half of the first and the second filler pass x-ray data records comprises only the x-ray data records of the arteries.

3. The method as claimed in claim 1, wherein a second half of the first and the second filler pass x-ray data records comprises only the x-ray data records of the veins.

4. The method as claimed in claim 1, wherein the mask pass comprises a rotation of the C-arms about 90° plus a half fan angle of the C-arms and the mask pass x-ray data record is recorded by both of the C-arms.

5. The method as claimed in claim 1, wherein the mask pass comprises a rotation of the C-arms about 180° plus a fan angle of the C-arms and the mask pass x-ray data records is recorded by one of the C-arms.

6. The method as claimed in claim 1, wherein a three-dimensional representation is reconstructed prior to the step of combining, or prior to the step of subtracting, or after the step of subtracting.

7. The method as claimed in claim 1, wherein the part of the body is a skull of the vertebrate.

8. A device for obtaining a separate x-ray data record of arteries or veins of a vascular system in a body part of a vertebrate using a biplanar C-arm system with a first C-arm and a second C-arm, comprising:

a device that injects a contrast agent into the vertebrate;

a control device that controls the first and the second C-arms so that:

a mask pass x-ray data record of the part of the body is recorded during a mask pass of the C-arm system rotating in a first direction about the part of the body prior to injecting the contrast agent, a first and a second filler pass x-ray data records of the part of the body is recorded respectively by the first and the second C-arms during one filler pass rotating in a second direction opposite to the first direction about the part of the body after injecting the contrast agent, wherein the first and the second C-arms are offset with respect to each other in the rotation direction by a differential angle; and a computing device that:

combines the first and the second filler pass x-ray data records to generate a first data record only comprising x-ray data records of the arteries and to generate a second data record only comprising x-ray data records of the veins, and subtracts the mask pass x-ray data record from the first or the second data record to obtain the separate data record of the arteries or the veins, wherein the filler pass comprises a configured to comprise a rotation of the C-arms about 180° plus a fan angle of the C-arms.

9. The device as claimed in claim 8, further comprising a data memory that stores the mask pass x-ray data record and the first and the second filler pass x-ray data records.

10. The device as claimed in claim 8, wherein the computing device reconstructs a three-dimensional representation prior to the combining, or prior to the subtracting, or after the subtracting.

11. The device as claimed in claim 8, wherein a first half of the first and the second filler pass x-ray data records comprises only the x-ray data records of the arteries.

12. The device as claimed in claim 8, wherein a second half of the first and the second filler pass x-ray data records comprises only the x-ray data records of the veins.

13. The device as claimed in claim 8, wherein the mask pass comprises a rotation of the C-arms about 90° plus a half fan angle of the C-arms and the mask pass x-ray data record is recorded by both of the C-arms.

14. The device as claimed in claim 8, wherein the mask pass comprises a rotation of the C-arms about 180° plus a fan angle of the C-arms and the mask pass x-ray data records is recorded by one of the C-arms.

15. The device as claimed in claim 8, wherein the part of the body is a skull of the vertebrate.

* * * * *